United States Patent
Seidel et al.

[11] Patent Number: 5,830,483
[45] Date of Patent: Nov. 3, 1998

[54] EMULSIONS

[75] Inventors: Kurt Seidel, Duesseldorf; Christian Priebe, Wuelfrath; Detlef Hollenberg, Erkrath, all of Germany

[73] Assignee: Henkel Kommanditgesellschaft auf Aktien, Duesseldorf, Germany

[21] Appl. No.: 702,483

[22] PCT Filed: Feb. 14, 1995

[86] PCT No.: PCT/EP95/00533

§ 371 Date: Sep. 12, 1996

§ 102(e) Date: Sep. 12, 1996

[87] PCT Pub. No.: WO95/22313

PCT Pub. Date: Aug. 24, 1995

[30] Foreign Application Priority Data

Feb. 22, 1994 [DE] Germany .......................... 44 05 510.2

[51] Int. Cl.$^6$ ............................ A61K 7/075; A61K 7/08; A61K 7/48; B01J 13/00
[52] U.S. Cl. ...................... 424/401; 252/312; 424/70.19; 424/70.31; 510/119; 510/417; 510/471; 514/941; 514/975
[58] Field of Search ........................ 252/312; 424/70.19, 424/70.31, 401; 514/941; 510/119, 471

[56] References Cited

U.S. PATENT DOCUMENTS

| | | | |
|---|---|---|---|
| 3,625,706 | 12/1971 | Myhre et al. | 426/555 |
| 4,330,526 | 5/1982 | Watanabe et al. | 424/70.19 |
| 4,565,647 | 1/1986 | Llenado | 510/119 X |
| 4,865,774 | 9/1989 | Fabry et al. | 510/428 |
| 4,931,218 | 6/1990 | Schenker et al. | 510/498 |
| 5,133,897 | 7/1992 | Balzer | 252/312 |
| 5,179,201 | 1/1993 | Oftring et al. | 510/471 |
| 5,294,726 | 3/1994 | Behler et al. | 554/98 |
| 5,358,667 | 10/1994 | Bergmann | 424/70.19 X |
| 5,603,940 | 2/1997 | Candau et al. | 424/401 |

FOREIGN PATENT DOCUMENTS

| | | |
|---|---|---|
| 512 270 | 11/1992 | European Pat. Off. . |
| 37 23 354 | 1/1989 | Germany . |
| 37 25 030 | 2/1989 | Germany . |
| 39 26 344 | 2/1991 | Germany . |
| 3 157 320 | 7/1991 | Japan . |

OTHER PUBLICATIONS

Cosmetic News, vol. 16, Dec. 1993, pp. 408–414.

*Primary Examiner*—Richard D. Lovering
*Attorney, Agent, or Firm*—Ernest G. Szoke; Wayne C. Jaeschke; Henry E. Millson, Jr.

[57] ABSTRACT

An oil-in-water emulsion comprising (A) from about 50 to about 99% by weight of water;
(B) from about 1 to about 30% by weight of an oil phase; and
(C) an emulsifying effective quantity of an emulsifier system consisting essentially of
   (i) at least one nonionic emulsifier of formula (I):

$$Z_x R^1 (R^2 - CO)_y G_z \qquad (I)$$

in which Z is a sugar unit selected from the group consisting of pentoses and hexoses, x is a number of 1 to 5, $R^1$ is a saturated alkyl radical containing 1 to 3 carbon atoms, $R^2$ is a linear or branched alkyl radical or mono- or polyunsaturated alkenyl radical containing 8 to 22 carbon atoms, y is the number 1 or 2, G is a polyglycerol residue consisting of 2 to 10 glycerol units and z is the number 1 or 2, and
   (ii) at least one ionic emulsifier selected from the group consisting of cationic and anionic emulsifiers.

17 Claims, No Drawings

EMULSIONS

This application is a 371 of PCT/EP95/00533 filed Feb. 14, 1995.

BACKGROUND OF THE INVENTION

1. Field of the Invention

This invention relates to oil-in-water emulsions containing special emulsifier combinations.

2. Statement of Related Art

Many compositions are now being formulated as oil-in-water emulsions. Accordingly, they generally consist of water, oil component(s), emulsifier(s) and a number of components required for the particular application envisaged. In addition, it is standard practice to adjust the physical properties and appearance of the emulsions as required by incorporating corresponding auxiliaries, for example thickeners.

For various reasons, it is nowadays an objective to simplify the formulations of such oil-in-water emulsions, i.e. to formulate the desired products with a smaller number of components. On the one hand, this has economic advantages and, on the other hand, can reduce the risk in other fields of application, for example cosmetics and pharmaceutical products, of sensitive people and people with allergies experiencing problems with individual components of the preparation.

DESCRIPTION OF THE INVENTION

It has now been found that oil-in-water emulsions with outstanding properties can be obtained by using special emulsifier combinations. It is surprising that, in many cases, these emulsions can be formulated without certain components, for example special thickeners, despite their high water content. In addition, the emulsifiers need only be used in small quantities in many cases, i.e. in quantities below 1% by weight, based on the emulsion.

Accordingly, the present invention relates to an oil-in-water emulsion containing 50 to 99% by weight of water and 1 to 30% by weight of oil phase, characterized in that it contains an emulsifier system (E) which consists of (A) a nonionic emulsifier corresponding to formula (I):

$$Z_x R^1 (R^2-CO)_y G_z \qquad (I)$$

In which Z is a sugar unit selected from pentoses and hexoses, x is a number of 1 to 5, $R^1$ is a saturated alkyl radical containing 1 to 3 carbon atoms, $R^2$ is a linear or branched alkyl radical or mono- or polyunsaturated alkenyl radical containing 8 to 22 carbon atoms, y is the number 1 or 2, G is a polyglycerol residue consisting of 2 to 10 glycerol units and z is the number 1 or 2, and (B) an ionic emulsifier selected from the group of cationic and anionic emulsifiers.

The nonionic emulsifiers (A) consist of structural elements obtained from natural renewable raw materials. They are therefore readily biodegradable and have advantageous ecological properties and thus meet the need to formulate products on the basis of renewable natural raw materials.

The core structural element of the emulsifiers (A) is a sugar unit selected from the hexoses and pentoses. Corresponding sugars are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose, glucose being particularly preferred. Although the hexoses and pentoses themselves are preferred structural units, it is also possible in accordance with the invention, if desired, to use emulsifiers (E) which contain corresponding oligosaccharides as their core structural unit. In such a case, the oligosaccharides are preferably composed of the same basic structural units. The oligosaccharides should be made up of at most 5 sugar units.

The sugar units are etherified with the alkyl radical of a short-chain alcohol and esterified with one or two long-chain, saturated or unsaturated fatty acids. The short-chain alkyl radical may be, in particular, the methyl radical or the ethyl radical. The methyl ethers are most particularly preferred. Suitable long-chain radicals $R^2$ are linear or branched alkyl radicals or mon- or polyunsaturated alkenyl radicals containing 8 to 22 carbon atoms. Preferred radicals are those which may be obtained from renewable raw materials, such as fats or oils. Radicals with chain lengths of 10 to 18 carbon atoms are particularly preferred. Groups $R^2$—CO derived, for example, from lauric, myristic, palmitic, stearic, oleic, linoleic or linolenic acid are preferred. Palmitoyl, oleoyl and, in particular, stearoyl groups are particularly preferred groups $R^2$—CO. In another preferred embodiment, the emulsifiers (A) contain two acyl groups $R^2$—CO, more especially two identical acyl groups $R^2$—CO. Mixtures of fatty alcohols obtained in the reduction of standard fats or oils, for example coconut oil, tallow, etc., may also be used for the production of the emulsifiers. In this case, $R^2$ may even represent a corresponding mixture of fatty alkyl radicals. Finally, the sugar units are etherified with one or two polyglycerol residues each consisting of 2 to 10 glycerol units and, more particularly, 2 to 5 glycerol units.

The ionic emulsifier (B) may be a cationic emulsifier or an anionic emulsifier.

Anionic emulsifiers are characterized by a water-solubilizing anionic group such as, for example, a carboxylate, sulfate, sulfonate or phosphate group and a lipophilic alkyl group containing around 10 to 22 carbon atoms. In addition, glycol or polyglycol ether groups, ester, ether and amide groups and also hydroxyl groups may be present in the molecule. The following are examples of suitable anionic emulsifiers—in the form of their sodium, potassium, magnesium and ammonium salts and also their mono-, di- and trialkanolammonium salts with 2 or 3 carbon atoms in the alkanol group:

linear fatty acids containing 10 to 22 carbon atoms (soaps), ether carboxylic acids corresponding to the formula R—O—(CH$_2$—CH$_2$O)$_x$—CH$_2$—COOH, in which R is a linear alkyl group containing 10 to 22 carbon atoms and x=0 or 1 to 16, acyl sarcosides containing 10 to 18 carbon atoms in the acyl group, acyl taurides containing 10 to 18 carbon atoms in the acyl group, acyl isethionates containing 10 to 18 carbon atoms in the acyl group, sulfosuccinic acid mono- and dialkyl esters containing 8 to 18 carbon atoms in the alkyl group and sulfosuccinic acid monoalkyl polyhydroxyethyl esters containing 8 to 18 carbon atoms in the alkyl group and 1 to 6 hydroxyethyl groups, linear alkanesulfonates containing 12 to 18 carbon atoms, linear α-olefin sulfonates containing 12 to 18 carbon atoms, α-sulfofatty acid methyl esters of fatty acids containing 12 to 18 carbon atoms, alkyl sulfates and alkyl polyglycol ether sulfates corresponding to the formula R—O(CH$_2$—CH$_2$O)$_x$—OSO$_3$H, in which R is a preferably linear alkyl group containing 10 to 18 carbon atoms and x=0 or 1 to 12, mixtures of surface-active hydroxysulfonates according to DE-A-37 25 030, sulfated hydroxyalkyl polyethylene and/or hydroxyalkylene propylene glycol ethers according to DE-A-37 23 354, sulfonates of unsaturated fatty acids containing 12 to 24 carbon atoms and 1 to 6 double bonds according to DE-A-39 26 344, esters of tartaric acid and citric acid with alcohols in the form of adducts of around 2 to 15 molecules of ethylene oxide and/or propylene oxide with fatty alcohols containing 8 to 22 carbon atoms.

Preferred anionic emulsifiers are alkyl sulfates, alkyl polyglycol ether sulfates and ether carboxylic acids containing 10 to 18 carbon atoms in the alkyl group and up to 12 glycol ether groups in the molecule.

The compounds containing alkyl groups used as ionic emulsifiers may be individual substances. In general, however, it is preferred to use native vegetable or animal raw materials in the production of these substances so that mixtures with different alkyl chain lengths, depending on the particular raw material, are obtained.

In the case of the ionic emulsifiers representing adducts of ethylene and/or propylene oxide with fatty alcohols or derivatives of these adducts, it is possible to use both products with a "normal" homolog distribution and those with a narrow homolog distribution. By "normal" homolog distribution are meant mixtures of homologs which are obtained in the reaction of fatty alcohol and alkylene oxide using alkali metals, alkali metal hydroxides or alkali metal alcoholates as catalysts. By contrast, narrow homolog distributions are obtained when, for example, hydrotalcites, alkaline earth metal salts of ether carboxylic acids, alkaline earth metal oxides, hydroxides or alcoholates are used as catalysts. It can be of advantage to use products with a narrow homolog distribution ("narrow-range" products).

Examples of cationic emulsifiers suitable for use in accordance with the invention are, in particular, quaternary ammonium compounds. Preferred cationic emulsifiers are ammonium halides, more especially chlorides and bromides, such as alkyl trimethylammonium chlorides, dialkyl dimethylammonium chlorides and trialkyl methylammonium chlorides, for example cetyl trimethylammonium chloride, stearyl trimethylammonium chloride, distearyl dimethylammonium chloride, lauryl dimethylammonium chloride, lauryl dimethyl benzylammonium chloride and tricetyl methylammonium chloride. Other cationic emulsifiers which may be used in accordance with the invention are the quaternized protein hydrolyzates or protein hydrolyzates derivatized with amino groups which are marketed, for example, under the names Lamequat® and Mackpro®.

Alkylamidoamines, more especially fatty acid amidoamines, such as the stearyl amidopropyl dimethylamine commercially available as Amid®S 18, are distinguished in particular by their ready biodegradability.

The readily degradable quaternary ester compounds, so-called "esterquats", such as the dialkylammonium methosulfates and methyl hydroxyalkyl dialkoylhydroxyalkyl ammonium methosulfates marketed as Stepantex® and Dehyquart®, for example N-methyl-N,N-bis-(acylhydroxyethyl)-N-(2-hydroxyethyl)-ammonium methosulfate, and the isostearamidopropyl morpholine lactate marketed as Mackalene®, may also be used in accordance with the invention.

Finally, cationic silicone oils are also suitable for the purposes of the invention. These include, for example, the commercially available products Q2-7224 (manufacturer: Dow Corning; a stabilized trimethyl silylamodimethicone), Dow Corning 929 Emulsion (containing a hydroxylamino-modified silicone which is also known as Amodimethicone), SM-2059 (manufacturer: General Electric), SLM-55067 (manufacturer: Wacker) and Abil®-Quat 3270 and 7232 (manufacturer: Th. Goldschmidt; diquaternary polydimethyl siloxanes, Quaternium-80).

One example of a quaternary sugar derivative suitable for use as a cationic emulsifier is the commercial product Glucquat®100 which bears the CTFA name of Lauryl Methyl Gluceth-10 Hydroxypropyl Dimonium Chloride.

Particularly preferred cationic emulsifiers are quaternary ammonium salts, alkyl amidoamines and quaternary ester compounds.

The nonionic emulsifiers (A) are present in the oil-in-water emulsions according to the invention in quantities of, preferably, 0.01 to 2.5% by weight and, more preferably, 0.05 to 1.0% by weight, based on the emulsion as a whole.

When the ionic emulsifiers (B) are anionic emulsifiers, they are preferably present in quantities of 0.1 to 10% by weight and, more preferably, in quantities of 0.5 to 5% by weight, again based on the emulsion as a whole.

When the ionic emulsifiers (B) are cationic emulsifiers, they are present in quantities of, preferably, 0.1 to 2% by weight and, more preferably, 0.4 to 0.8% by weight, again based on the emulsion as a whole.

Another compulsory component is the oil phase which is present in the emulsions according to the invention in quantities of 1 to 30% by weight and, more particularly, 1 to 15% by weight, based on the emulsion as a whole.

Suitable oils are, for example, mono-, di- and triglycerides and mixtures thereof, paraffin oils, fatty alcohols, fatty alkyl alkanolamides, silicone oils, esters of fatty acids with lower alcohols, esters of fatty acids with fatty alcohols and dialkyl ethers containing 6 to 20 carbon atoms in the alkyl chain.

The emulsions according to the invention may be used as a base for cosmetic and pharmaceutical preparations. This emulsion base has proved to be of particular advantage for the formulation of skin treatment and hair treatment preparations. These preparations are distinguished by a rich appearance and by very good flow behavior. Their viscosity may be adjusted to the required values with only comparatively small quantities of emulsifier.

These preparations may contain any of the active substances, auxiliaries and additives known to the expert which are described in detail in the monographs known to the expert (for example K. Schrader, Grundlagen und Rezepturen der Kosmetik, Hüithig Buchverlag, Heidelberg). For hair treatment preparations, these active substances, auxiliaries and additives are, for example, zwitterionic surfactants, for example betaines, ampholytic surfactants, nonionic surfactants, for example alkyl polyglycosides and ethoxylated fatty alcohols, cationic polymers, such as quaternized cellulose ethers, polysiloxanes containing quaternary groups, dimethyl diallylammonium chloride polymers, acrylamide dimethyl diallylammonium chloride copolymers, dimethyl aminoethyl methacrylate/vinyl pyrrolidone copolymers quaternized with diethyl sulfate, vinyl pyrrolidone/methoimidazolinium chloride copolymers and quaternized polyvinyl alcohol, anionic polymers such as, for example, vinyl acetate/crotonic acid copolymers, vinyl acetate/butyl maleate/isobornyl acrylate copolymers, methyl vinyl ether/maleic anhydride copolymers and esters thereof and also uncrosslinked and polyol-crosslinked polyacrylic acids, zwitterionic and amphoteric polymers such as, for example, acrylamidopropyl trimethylammonium chloride/acrylate copolymers, octyl acrylamide/methyl methacrylate/tert.butyl aminoethyl methacrylate/2-hydroxypropyl methacrylate copolymers, nonionic polymers such as, for example, polyvinyl pyrrolidone, vinyl pyrrolidone/vinyl acetate copolymers and cellulose ethers, structurants such as glucose and maleic acid, hair-conditioning compounds, such as phospholipids, for example soya lecithin, egg lecithin and kephalins, and silicone oils, protein hydrolyzates, more especially elastin, collagen, keratin, milk protein, soya protein and wheat protein hydrolyzates, condensates thereof with fatty acids, perfume oils, dimethyl isosorbide and cyclodextrins, solubilizers, such as ethanol, isopropanol, ethylene glycol, propylene glycol, glycerol and diethylene glycol, dyes, anti-dandruff agents, such as Piroctone Olamine and Zinc Omadine, other substances for adjusting the pH value, active substances, such as panthenol, allantoin, pyrrolidone carboxylic acids and salts thereof, vegetable extracts and vitamins, light stabilizers, consistency regulators, such as sugar esters, polyol esters and polyol alkyl ethers, waxes, such as spermaceti, beeswax and montan wax, complexing agents, such as EDTA, NTA and phosphonic acids, swelling agents and penetration agents, such as glycerol, propylene glycol monoethyl ether, carbonates, hydrogen carbonates, guanidines, ureas and primary, secondary and tertiary phosphates, opacifiers, such as latex, pearlescers, such as ethylene glycol mono- and distearate, propellents, such as propane-butane mixtures, $N_2O$, dimethyl ether, $CO_2$ and air and antioxidants, substantive dyes, so-called primary and secondary intermediates as oxidation dye precursors, reducing agents, for example thioglycolic acid and derivatives thereof, thiolactic acid, cysteamine, thiomalic acid and α-mercaptoethane sulfonic acid, oxidizing agents, such as hydrogen peroxide, potassium bromate and sodium bromate.

The hair treatment preparations according to the invention are preferably rinses, shampoos and tonics. However, the combination of active substances according to the invention may also be used in other hair treatment preparations, for example coloring and tinting shampoos or creams, hair colorants, and in permanent waving.

The hair treatment preparations according to the invention may remain on the hair or may be removed from the hair after a certain contact time of, generally, a few seconds to around 20 minutes.

Accordingly, the present invention also relates to the use of the oil-in-water emulsion according to the invention for the treatment of skin and/or hair.

The following Examples are intended to illustrate the invention.

EXAMPLES

1. Investigations into the Formation and Properties of Emulsions

The following components were used:

Fats or oils:

F1: paraffin oil perliquidum

F2: Cutina® GMS[1]

F3: Lanette® 16[2]

[1] Glycerol monostearate (CTFA name: Glyceryl Stearate) (HENKEL)
[2] C16 fatty alcohol (CTFA name: Cetyl Alcohol) (HENKEL)

Emulsifiers:

A1: Tego® Care 450[3]

AV: Aminol® N[4] (for comparison)

B1: Dehyquart®A[5]

B2: Tego®Amid S 18[6]

B3: Mackalene® 426[7]

B4: Texapon® N 25[8]

[3] Methyl glucoside distearic acid ester, etherified with polyglycerol (CTFA name (applied for): Polyglycerol Methyl Glucose Distearate) (GOLDSCHMIDT)
[4] Ethoxylated fatty acid monoethanolamide based on rape seeds (CTFA name: PEG-4 Rapeseedamide) (CHEM-Y)
[5] Trimethyl hexadecylammonium chloride (CTFA name: Cetrimonium Chloride; approximately 25% active substance in water) (HENKEL)
[6] N,N-dimethyl-N'-stearoyl-1,3-diaminopropane (CTFA name: Stearamidopropyl Dimethylamin) (GOLDSCHMIDT)
[7] Lactic acid salt of isostearamidopropyl morpholine (CTFA name Isostearamidopropylmorpholine Lactate; approximately 25% of active substance) (McINTYRE)
[8] Sodium lauryl ether sulfate (approximately 28% of active substance; CTFA name: Sodium Laureth Sulfate) (HENKEL)

The results obtained are set out in Table 1:

TABLE 1

| Component/mixture | C1 | C2 | B1 | C3 | C4 | B2 | C5 | C6 | B3 | C7 | C8 |
|---|---|---|---|---|---|---|---|---|---|---|---|
| Fat/Oil: | | | | | | | | | | | |
| F1 | 3.0 | 3.0 | 3.0 | — | — | — | — | — | — | — | — |
| F2 | — | — | — | 3.0 | 3.0 | 3.0 | — | — | — | — | — |

TABLE 1-continued

[Quantities in Parts by Weight]

| | | | | | | | | | | | |
|---|---|---|---|---|---|---|---|---|---|---|---|
| F3 | — | — | — | — | — | — | 3.0 | 3.0 | 3.0 | 3.0 | 3.0 |
| Emulsifiers: | | | | | | | | | | | |
| A1 | 0.2 | — | 0.1 | 0.2 | — | 0.1 | 0.2 | — | 0.1 | — | — |
| AV | — | — | — | — | — | — | — | — | — | 0.2 | 0.1 |
| B1 | — | 0.8 | 0.4 | — | 0.8 | 0.4 | — | 0.8 | 0.4 | — | 0.4 |
| B2 | — | — | — | — | — | — | — | — | — | — | — |
| B3 | — | — | — | — | — | — | — | — | — | — | — |
| B4 | — | — | — | — | — | — | — | — | — | — | — |
| Water | | | | ←————— | ad 100 | —————→ | | | | | |
| Emulsion | No | No | Yes | No | Yes | Yes | Pe* | Yes | Yes | No | Pe* |
| $t_o$ [mPas]$^a$ | — | — | 200 | — | 1200 | 1800 | — | 200 | 400 | — | — |
| $t_1$ [mPas]$^b$ | — | — | 500 | — | 2100 | 2700 | — | 400 | 1000 | — | — |

| Component/mixture | C9 | C10 | B4 | C11 | B5 | C12 | B6 | C13 | B7 |
|---|---|---|---|---|---|---|---|---|---|
| Fat/Oil: | | | | | | | | | |
| F1 | — | — | — | — | — | — | — | — | — |
| F2 | 1.5 | 1.5 | 1.5 | — | — | — | — | — | — |
| F3 | 1.5 | 1.5 | 1.5 | 3.0 | 3.0 | 3.0 | 3.0 | 3.0 | 3.0 |
| Emulsifiers: | | | | | | | | | |
| A1 | 0.2 | — | 0.1 | — | 0.1 | — | 0.1 | — | 0.1 |
| AV | — | — | — | — | — | — | — | — | — |
| B1 | — | 0.8 | 0.4 | — | — | — | — | — | — |
| B2 | — | — | — | 0.2 | 0.1 | — | — | — | — |
| B3 | — | — | — | — | — | 0.8 | 0.4 | — | — |
| B4 | — | — | — | — | — | — | — | 0.8 | 0.4 |
| Water | | | ←————— | ad 100 | —————→ | | | | |
| Emulsion | No | Yes | Yes | Pe* | Yes | Pe* | Yes | Yes | Yes |
| $t_o$ [mPas]$^a$ | — | 600 | 900 | — | 500 | — | 200 | 800 | 1200 |
| $t_1$ [mPas]$^b$ | — | 1100 | 1500 | — | 800 | — | — | 2400 | 2900 |

$^a$Viscosity immediately after preparation, as measured with a Brookfield type RVF viscosimeter, spindle 4, 10 r.p.m.
$^B$Viscosity after 24 h, as measured with a Brookfield type RVF viscosimeter, spindle 4, 20 r.p.m.
*Partly emulsified

2. Application Examples

All quantities are in parts by weight.

2.1. Hair Tonic

| | |
|---|---|
| Cutina ®GMS | 0.3 |
| Lanette ® 16 | 4.8 |
| Paraffin oil perliq. | 3.9 |
| Cetiol ®OE$^9$ | 0.2 |
| Tego Care ®450 | 0.4 |
| Dehyquart °A | 3.0 |
| Dehyquart ®AU 46$^{10}$ | 1.0 |
| Luvisko ®K 30$^{11}$ | 1.0 |
| Lamequat ®L$^{12}$ | 0.3 |
| Culminal ® MHPC 3000$^{13}$ | 0.6 |
| Preservative | q.s. |
| Water | ad 100 |

2.2. Cleaning Milk

| | |
|---|---|
| Lanette ®16 | 3.0 |
| Cetiol ®SN$^{14}$ | 2.5 |
| Texapon ®N 25$^{15}$ | 15.0 |
| Plantaren ®1200 UP$^{16}$ | 3.0 |
| Tego Care ®450 | 0.15 |
| Myritol ®318$^{17}$ | 1.8 |
| Proteol ®VS 22$^{18}$ | 2.0 |
| Preservative | q.s. |
| Water | ad 100 |

2.3. Hair Rinse

| | |
|---|---|
| Lanette ®16 | 3.0 |
| TegoAmid ®S 18$^{19}$ | 1.2 |
| Dehyquart ®AU 46 | 0.5 |
| Tego Care ®450 | 0.2 |
| Natrosol ®250 HR$^{20}$ | 0.7 |
| Citric acid | 0.2 |
| Preservative | q.s. |
| Water | ad 100 |

$^9$Dioctyl ether (CTFA name: Dicapryl Ether) (HENKEL)
$^{10}$N-Methyl-N,N-bis-(acylhydroxyethyl)-N-(2-hydroxyethyl)-ammonium methosulfate (approximately 90% of active substance in isopropanol) (HENKEL)
$^{11}$Polyvinyl pyrrolidone (CTFA name: PVP) (BASF)
$^{12}$Cationized collagen hydrolyzate (approximately 35% of active substance; CTFA name: Lauryldimonium Hydroxypropyl Hydrolyzed Collagen) (HENKEL)
$^{13}$Methylhydroxypropyl cellulose (AQUALON)
$^{14}$Cetostearyl isononanoate (CTFA name: Cetearyl Isononanoate) (HENKEL)
$^{15}$Sodium lauryl ether sulfate (approximately 28% of active substance; CTFA name: Sodium Laureth Sulfate) (HENKEL)
$^{16}$C$_{12-16}$ Alkyl glucoside with a degree of oligomerization of 1.4 (approximately 50% of active substance; CTFA name: Lauryl Polyglycose) (HENKEL)
$^{17}$Fatty acid triglyceride (CTFA name: Caprylic Capric Triglyceride) (HENKEL)
$^{18}$Soya protein hydrolyzate cocofatty acid sodium salt (approximately 22% of active substance; CTFA name: Sodium Cocoyl Hydrolyzed Soy Protein) (SEPPIC)
$^{19}$N,N-Dimethyl-N'-stearoyl-1,3-diaminopropane (CTFA name: Stearamidopropyl Dimethylamin) (GOLDSCHMIDT)
$^{20}$Hydroxyethyl cellulose (AQUALON)

We claim:

1. An oil-in-water emulsion consisting essentially of
   (A) from about 50 to about 99% by weight of water;
   (B) from about 1 to about 30% by weight of an oil phase; and
   (C) an emulsifying effective quantity of an emulsifier system consisting essentially of
      (i) at least one nonionic emulsifier of formula (I):

$$Z_xR^1(R^2\text{—CO})_yG_z \qquad (I)$$

in which Z is a sugar unit selected from the group consisting of pentoses and hexoses, x is a number of 1 to 5, $R^1$ is a saturated alkyl radical containing 1 to 3 carbon atoms, $R^2$ is a linear or branched alkyl radical or mono- or polyunsaturated alkenyl radical containing 8 to 22 carbon atoms, y is the number 1 or 2, G is a polyglycerol residue consisting of 2 to 10 glycerol units and z is the number 1 or 2, and (ii) at least one ionic emulsifier selected from the group consisting of cationic and anionic emulsifiers.

2. The oil-in-water emulsion of claim 1 wherein component (C)(ii) is at least one cationic emulsifier selected from the group consisting of quaternary ammonium compounds, alkylamidoamines and quaternary ester compounds.

3. The oil-in-water emulsion of claim 2 wherein in component (C)(i), Z is glucose, x=1, $R^1$ is a methyl group, $R^2$ is a linear or branched alkyl radical or mono- or polyunsaturated alkenyl radical containing 10 to 18 carbon atoms, y=2 and $G_z$ is a polyglycerol residue consisting of from 2 to 5 glycerol units.

4. The oil-in-water emulsion of claim 1 wherein component (C)(ii) is at least one anionic emulsifier selected from the group consisting of fatty alkyl polyglycol ether sulfates, fatty alkyl sulfates and fatty alkyl polyglycol ether carboxylates.

5. The oil-in-water emulsion of claim 4 wherein in component (C)(i), Z is glucose, x=1, $R^1$ is a methyl group, $R^2$ is a linear or branched alkyl radical or mono- or polyunsaturated alkenyl radical containing 10 to 18 carbon atoms, y=2 and $G_z$ is a polyglycerol residue consisting of from 2 to 5 glycerol units.

6. The oil-in-water emulsion of claim 1 wherein in component (C)(i), Z is glucose, x=1, $R^1$ is a methyl group, $R^2$ is a linear or branched alkyl radical or mono- or polyunsaturated alkenyl radical containing 10 to 18 carbon atoms, y=2 and $G_z$ is a polyglycerol residue consisting of from 2 to 5 glycerol units.

7. The oil-in-water emulsion of claim 1 wherein in component (C)(i), z is the sugar unit selected from the group consisting of glucose, fructose, galactose, arabinose and sucrose.

8. The oil-in-water emulsion of claim 7 wherein in component (C)(i), $R^1$ is methyl or ethyl.

9. The oil-in-water emulsion of claim 8 wherein in component (C)(i), $R^2$ contains from 10 to 18 carbon atoms.

10. The oil-in-water emulsion of claim 9 wherein in component (C)(i), G consists of from 2 to 5 glycerol units.

11. The oil-in-water emulsion of claim 1 wherein component (C)(i) is present in from about 0.05 to about 1.0% by weight.

12. The oil-in-water emulsion of claim 1 wherein when component (C)(ii) is a cationic emulsifier, it is present in from about 0.4 to about 0.8% by weight, based on the weight of the emulsion, and when component (C)(ii) is an anionic emulsifier, it is present in from about 0.5 to about 5% by weight, based on the weight of the emulsion.

13. The oil-in-water emulsion of claim 1 wherein component (B) is at least one oil selected from the group consisting of mono-, di- and triglycerides and mixtures thereof, paraffin oils, fatty alcohols, fatty alkyl alkanolamides, silicone oils, esters of fatty acids with lower alcohols, esters of fatty acids with fatty alcohols, and dialkyl ethers containing 6 to 20 carbon atoms in the alkyl chain.

14. The oil-in-water emulsion of claim 1 wherein component (B) is present in from about 1 to about 15% by weight.

15. In a cosmetic or pharmaceutical composition, the improvement wherein the oil-in-water emulsion of claim 1 is present therein.

16. The composition of claim 15 wherein the composition is a cosmetic formulation for the treatment of hair and/or skin.

17. A method for the treatment of hair and/or skin comprising applying thereto the composition of claim 15.

* * * * *